United States Patent
Merz (10) Patent No.: US 8,669,124 B2
(45) Date of Patent: Mar. 11, 2014

(54) APPARATUS AND METHOD FOR MOLECULE DETECTION USING NANOPORES

(75) Inventor: Matthias Merz, Leuven (BE)

(73) Assignee: NXP, B.V., Eindhoven (NL)

( * ) Notice: Subject to any disclaimer, the term of this patent is extended or adjusted under 35 U.S.C. 154(b) by 322 days.

(21) Appl. No.: 13/059,410

(22) PCT Filed: Aug. 12, 2009

(86) PCT No.: PCT/IB2009/053560
§ 371 (c)(1),
(2), (4) Date: Feb. 16, 2011

(87) PCT Pub. No.: WO2010/020912
PCT Pub. Date: Feb. 25, 2010

(65) Prior Publication Data
US 2011/0133255 A1    Jun. 9, 2011

(30) Foreign Application Priority Data
Aug. 20, 2008 (EP) .................... 08105086

(51) Int. Cl.
*H01L 21/66* (2006.01)
*H01L 29/66* (2006.01)

(52) U.S. Cl.
USPC ............. 438/18; 438/49; 257/239; 257/253; 257/266

(58) Field of Classification Search
None
See application file for complete search history.

(56) References Cited

U.S. PATENT DOCUMENTS

| | | | |
|---|---|---|---|
| 6,627,067 B1* | 9/2003 | Branton et al. | 205/778 |
| 7,001,792 B2* | 2/2006 | Sauer et al. | 438/49 |
| 7,410,564 B2* | 8/2008 | Flory | 205/777.5 |
| 8,232,582 B2* | 7/2012 | Sauer et al. | 257/239 |
| 8,426,232 B2* | 4/2013 | Sauer et al. | 438/49 |
| 2002/0127855 A1 | 9/2002 | Sauer et al. | |
| 2003/0104428 A1 | 6/2003 | Branton et al. | |
| 2005/0102721 A1 | 5/2005 | Barth | |
| 2006/0275778 A1 | 12/2006 | Wu et al. | |
| 2010/0066348 A1* | 3/2010 | Merz et al. | 324/71.1 |

FOREIGN PATENT DOCUMENTS

| EP | 1433744 A1 | 6/2004 |
|---|---|---|
| EP | 1486775 A1 | 12/2004 |

OTHER PUBLICATIONS

Hofmann, Franz, et al; "Passive DNA Sensor with Gold Electrodes Fabricated in a CMOS Backend Process"; Solid-State Device Research Conference; 4 pages (Sep. 2002).
Hofmann, Franz, et al; "Technology Aspects of a CMOS Neuro-Sensor: Back End Process and Packaging"; European Solid-State Device Research 2003; 4 pages (Sep. 2003).
Kohler, Michael; "Etching in Microsystem Technology"; Wiley-VCH; pp. 98-103, 158-161, 176-177 (1999).
International Search Report for application No. PCT/IB2009/053560 dated Nov. 12, 2009.

* cited by examiner

*Primary Examiner* — Alonzo Chambliss (57) ABSTRACT

A detector device and method of its fabrication are disclosed. Illustratively, an additional via is present through an insulator layer over a gate channel region which is on top of the channel region. The additional via is filled with conductor material. The conductor material is removed to form a chamber leading to one side of the gate channel region. Furthermore, a nanopore is etched from the chamber through the channel region.

15 Claims, 8 Drawing Sheets

APPARATUS AND METHOD FOR MOLECULE DETECTION USING NANOPORES

This invention relates to nanopore molecule detectors and manufacturing methods, for example for use in detecting DNA nucleotide monomers.

DNA is a double helix consisting of two strands of molecules. Each strand is formed as a chain of the four nucleotides adenine (A), thymine (T), cytosine (C) and guanine (G). The order or sequence of these nucleotides encodes all information for metabolism and reproduction in any living organism. In humans each DNA strand consists of more than 3 Billion nucleotides.

Knowing the DNA sequence of a species is interesting from a basic research point of view but also offers many possibilities in medicine such as early detection of diseases and the development of new vaccines and drugs. DNA fingerprint detection from individuals has become a standard-technique in criminology. With these many applications, DNA sequencing, i.e. determining the nucleotide order in a DNA strand, has become a big market for equipment manufacturers as well as service providers.

The chain termination method (developed by F. Sanger) is the state-of-the-art technique for DNA sequencing. Recently two new techniques, "pyrosequencing" and "454 Sequencing" (from the company 454) have been introduced. Despite major differences in sample preparation and detection (chain termination uses electrophoresis for DNA fragment separation and dye or radioactive labels, whereas pyrosequencing and 454 Sequencing are based on chemiluminiscent enzymatic reactions when a nucleotide is incorporated into the DNA strand during replication), all techniques rely on the amplification of the initial amount of DNA by polymerase chain reaction (PCR). Moreover, they also use PCR in the sequencing process itself.

Therefore, chain termination, pyrosequencing and 454 sequencing are all affected by the limitations of PCR (e.g. primer annealed to a second site, RNA contamination acting as primer, reading problems associated with the secondary structure of DNA). Due to these and other constraints, sequencing machines based on the chain termination method can detect a maximum of about 1000 nucleotides, and 454 sequencing can detect only around 100 nucleotides. This has serious disadvantages for whole genome assembly especially for highly repetitive genomes, when genome assembly is ambiguous. PCR is also a rather slow process due to cycling steps at specific temperatures and requires large amounts of (expensive) chemicals.

Alternative sequencing techniques are heavily investigated at universities and in the industry, aiming to not rely on PCR. However, none of them has produced good results so far.

Nanopore sequencing is one of the most favored new techniques, for example as described in US20050102721(A1) and US20030104428(A1).

A DNA molecule is 'pulled' through a thin pore with a diameter in the order of a few nanometer by electrophoresis (in most experiments a solid state pore is used, but also transmembrane proteins in a lipid bilayer have been investigated).

Figure 1:
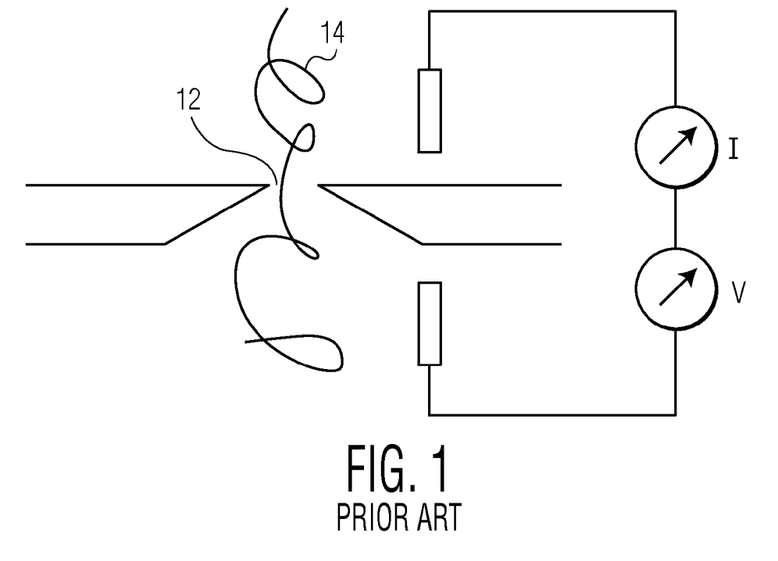
FIG. 1 shows in simplified form a known nanopore detector.

FIG. 1 shows the basic operating principle of conventional nanopore sequencing.

A voltage bias across a membrane causes ions to flow through the nanopore 12 between two ion-containing solutions. By drawing polymers of DNA 14 though the nanopore, the number of ions that pass through is reduced, and this is detected as a change in current.

Ideally, the DNA passes the pore one nucleotide at the time, each nucleotide blocking the current through the pore in a characteristic manner. The sequence of current readings directly represents the DNA sequence. In order to be accurate, the pore diameter must be very small (about the size of a nucleotide) so that a single nucleotide can block the current and it must be sufficiently thin to assure that the signal is modulated by a single nucleotide rather than several.

Figure 2:
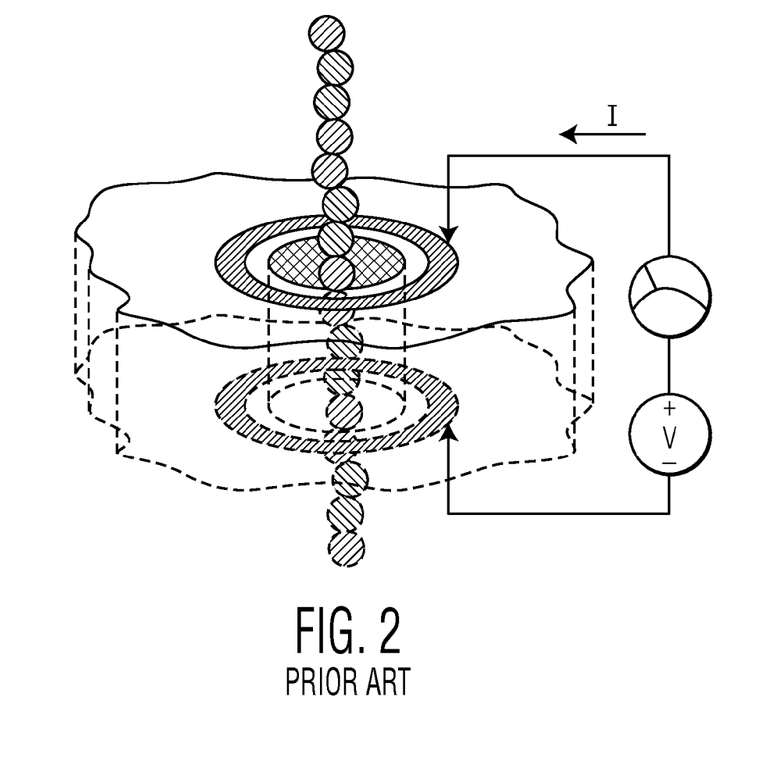
FIG. 2 shows the configuration of a known type of nanopore detector.

EP1486775(A1) discloses a nanopore device with two electrodes fabricated at the two sides of the pore. Sequence information is conveyed in the tunnel current between these electrodes as the DNA strand is gradually pulled through the pore. The arrangement is shown in FIG. 2.

Figure 3:
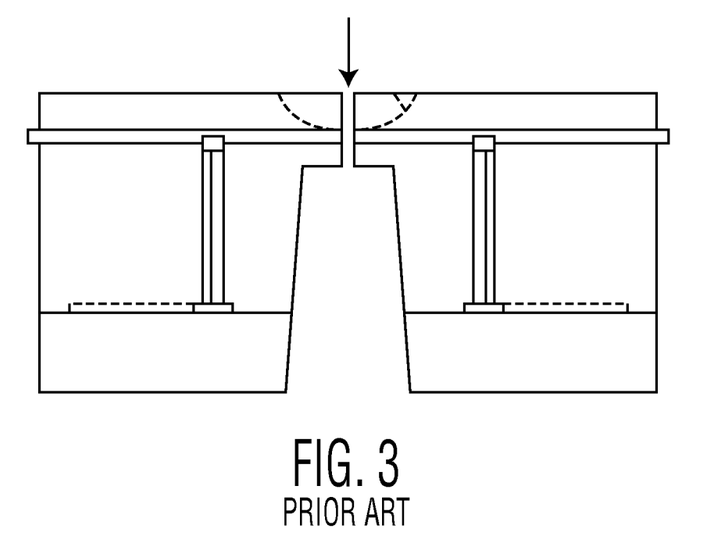
FIG. 3 shows the configuration of another known type of nanopore detector.

Similarly, EP1433744(A1) discloses a nanotube embedded in a substrate with a nanopore processed through the tube and substrate. DNA is sequenced by pulling the strand through the pore and measuring the current between the two parts of the tube when a voltage is applied. The structure is shown in FIG. 3. In this configuration, two voltages are applied—one between the left and right side of the nanotube for obtaining the sequence (e.g. tunnel current across nucleotides), the other in parallel to the pore for pulling the DNA strand through the pore.

The applicant has proposed (but not published at the time of filing this application) a detector device having a nanopore which passes through a channel region, and which connects fluid chambers on opposite sides of the nanopore. A voltage bias is provided between the fluid chambers, and between source and drain regions. A current sensor senses a charge flow between the source and drain regions.

This device uses a nanopore for the confinement of a sample under test (for example nucleotides of a DNA strand) close to a sensor. The size of the sensor can be made similar to the spacing of adjacent nucleotides. In this way, the disadvantages of PCR based techniques are avoided, and single nucleotide resolution can be attained. The device can provide direct contact between the sensor and the sample under test, so that signal disturbance by stray capacitances and resistances are minimized.

In one implementation, there is provided the integration of a nanopore in the gate area of a structure corresponding to a field-effect-transistor (FET). The conducting inversion layer of such a device has a thickness in the (sub) nanometer range which makes it an ideal sensor for sequencing nucleotides which are only separated by 0.34 nm in a DNA strand.

Etching of small pores with diameters of less than 10 nm and very high aspect ratios above ten is a major challenge in the manufacturing of these devices. While such small structures can be written with e-beam lithography they are difficult to implement with standard CMOS process technology. With state-of-the-art optical lithography equipment, feature sizes in the range of 50 nm can be reached for such a hole. The applicant has proposed further reduction of the aperture of this hole by means of spacers, a standard process module in the production of MOS transistors.

However, the etch process to provide access to the location where the nanopore is to be formed is very difficult, especially if the device uses many metal layers as interconnect layers. Several micrometers of dielectrics of various composition must be removed, and the diameter of the access hole must be very small (near the gate less than around 200 nm) and stop directly on the gate. Moreover, exact alignment of the etch mask could be problematic due to the large distance between the passivation stack (final layer) and gate. The alignment accuracy must be good enough to center on the gate, for example better then 50 nm.

According to the invention, there is provided a method of fabricating a detector device, comprising:

forming a source region, a drain region and a gate contact on a substrate, with a channel region between the source and drain regions;

forming an insulator layer over the substrate;

forming first vias through the insulator layer and filling the vias with conductor material, wherein the first vias are provided over the source and drain regions and the gate contact;

wherein the method further comprises:

forming an additional via through the insulator layer over a gate channel region which is on top of the channel region, and filling the additional via with said conductor material;

removing the conductor material filling from the additional via to form a first chamber leading to a first side of the gate channel region, and wherein the method further comprises etching a nanopore from the first chamber through the channel region.

This method forms a via to define a channel/chamber leading to the gate using the same process steps as used to form other at least one other via, required for connection to the source, gate or drain contacts. Thus, the chamber can be defined using standard processing steps. The formation of the nanopore can then be at the end of the production process, and only the formation of the nanopore itself needs to be implemented using additional processing steps.

This process essentially uses metal interconnect structures as dummies for the selective etch of the chamber, which functions as an access structure.

The nanopore can for example be etched through to the opposite side of the substrate. In this case, the method can further comprise locally thinning the substrate at the gate channel region to form a second chamber opposite the first chamber. This reduces the required length of the nanopore.

The method can further comprise forming fluid chambers on opposite sides of the nanopore and filling them with electrolyte; connecting drive means to the fluid chambers; connecting drive means to the source and drain regions; and providing a current sensor for sensing a charge flow between the source and drain regions. This defines the required components for the sensing function.

A dielectric liner can be formed in the first chamber before etching the nanopore. This protects the side walls of the chamber from the electrolyte which will be in the chamber as part of the nanopore etching process and during operational use of the device. The dielectric liner can be etched to remove a portion of the dielectric liner at the location where the nanopore is to be formed. This etch process can be used to define a very narrow opening in the dielectric layer, which can be used as a mask for the nanopore forming process.

The nanopore can be formed by a wet etch process, for example electrochemical etching. Alternatively, or additionally, the nanopore can be formed by particle trace etching. Trace etching or field assisted etching techniques enable high aspect ratio nanopores to be formed.

Forming an insulator layer can comprise forming a stack of insulator layers and conductor layers, thereby providing multiple isolated conductor layers. These can be part of a standard CMOS process.

The invention also provides a detector device, comprising:
a substrate;
a source region, a drain region and a gate contact on the substrate;
a channel region between the source and drain regions;
a gate on top of the channel region;
an insulator layer over the substrate;
first vias through the insulator layer filled with conductor material, wherein the first via is provided over the source and drain region and gate contact,
an additional via through the insulator layer over the gate, the additional via defining a chamber leading to a first side of the gate channel region,
a nanopore which passes through the channel region, and which connects fluid chambers on opposite sides of the nanopore;
drive means for providing a voltage bias between the fluid chambers;
drive means for providing a voltage between the source and drain regions and gate; and
a current sensor for sensing a charge flow between the source and drain regions.

The invention will now be described in detail with reference to the accompanying drawings, in which.

The invention relates to the manufacture of a device which incorporates a nanopore into the structure corresponding to the gate of a transistor, for example a field effect transistor or a quantum well transistor device. The structure of the device will first be described, before the method of the invention is described in detail.

Figure 4:
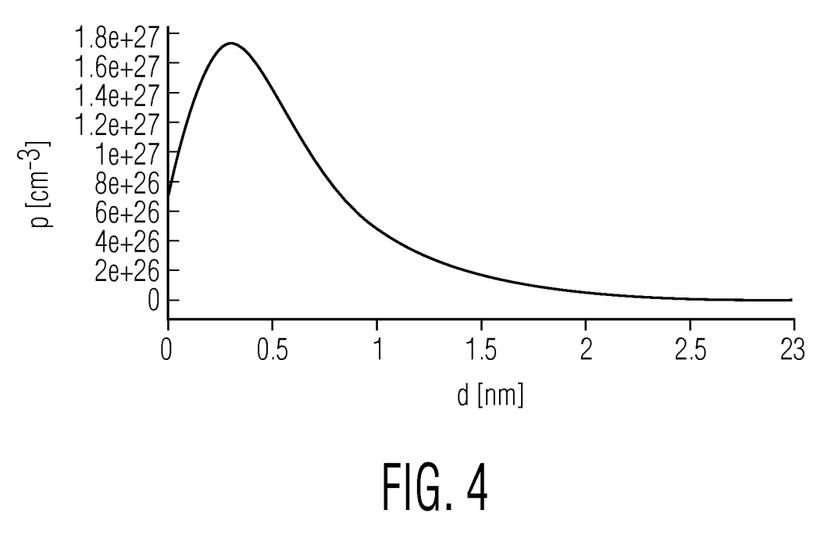
FIG. 4 shows the charge density plot for an inversion channel.

The conducting inversion layer of a FET transistor has a thickness in the (sub) nanometer range, which makes it the ideal sensor for sequencing nucleotides which are only separated by 0.34 nm in a DNA strand. FIG. 4 shows the charge density plot for an inversion channel. In FIG. 4, d denotes the distance in nm from the silicon/oxide interface. The width of the peak at half maximum is clearly below 1 nm.

Figure 5A:
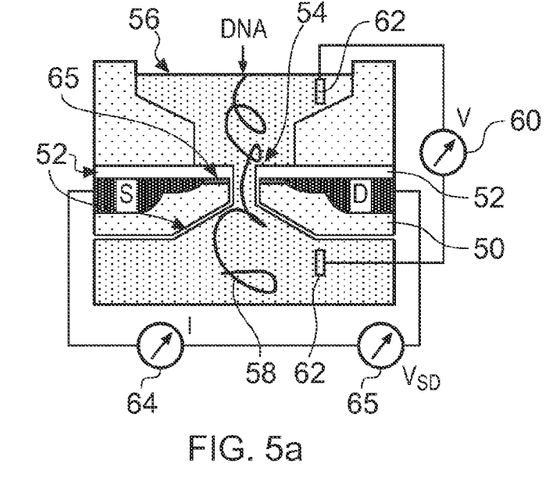
FIGS. 5a to 5f shows first examples of device as proposed by the applicant.
Figure 5B:
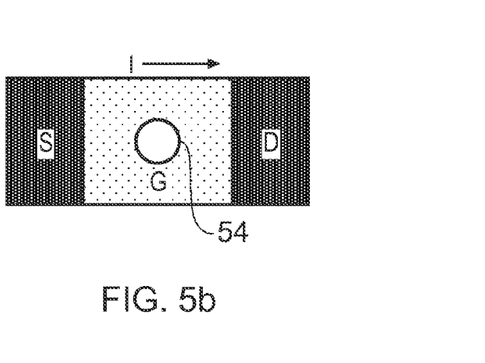

FIG. 5a shows the operating principle of a first example of nanopore FET for DNA sequencing, which can be manufactured using the method of the invention. A top view is shown in FIG. 5b, with source (S) drain (D) and gate (G) indicated, and the position of the nanopore 54.

FIG. 5a is an example with no gate contact, and is described first as there are less components in the design. Thus, the structure is slightly different to a conventional transistor. A preferred example is described with reference to FIG. 5a below, which based more closely on a conventional transistor layout.

As shown in FIG. 5a, the device corresponds to a field effect transistor having a substrate 50 with source and drain regions S,D, and an overlying gate oxide layer 52. An oxide layer 53 can also be provided as a protective dielectric on the backside of the transistor.

In the following description, even for the design of FIG. 5a, the structure is referred to as a transistor, because it has a number of features in common with a transistor, but has a different gate design, as in this example there is no patterned gate electrode. The use of the term "transistor" should be understood accordingly. The structure can, however, be manufactured with minor modification or additional steps to conventional transistor manufacturing processes.

The channel area of the transistor extends between the source and drain, and is provided with a nanopore 54. The nanopore couples upper and lower chambers 56,58 which contain electrolyte. The nanopore has a diameter only slightly larger than the size of the nucleotides (i.e. smaller than 5 nm).

The gate voltage of the transistor is provided by the electrolyte voltage of the upper chamber, rather than by a patterned gate electrode. Other than this, the structure of the transistor is conventional, and many different FET designs can be used.

A voltage bias is provided between the fluid chambers by a voltage source 60 associated with electrodes 62, and a current sensor 64 enables sensing of the source-drain current of the transistor. A further voltage source 65 ($V_{SD}$) also provides a source drain voltage. A further voltage source may be used for controlling the bulk voltage (not shown).

The DNA is moved through the nanopore 54 by applying a voltage between the top and bottom chambers of the cell. This voltage also acts as the gate voltage and sets the working point of the transistor. The nucleotides passing the nanopore modulate the source-drain current if they are in close proximity to the channel.

With this design, the resolution and sensitivity can be so high that individual nucleotides can be detected.

Since the sensitive area of the detector (in vertical direction) is limited to the thickness of the inversion layer, the nanopore can be much longer than in the conventional nanopore devices described above. The sequencing is based on modulation of the source-drain current not by measuring the current through the pore (although synchronous measurement of both currents may be useful for voltage control and feedback).

In principle two effects can contribute to the modulation of the source-drain current:

Nucleotides with different charges can modulate the gate voltage. Many experimental and theoretical studies have been done on the electron affinity of DNA nucleotides. The electron affinity is the amount of energy required to add an electron to a neutral atom in the gas phase to form an ion. The concept also applies to molecules and gives information about their behavior in solution. Although a large range of different values derived from theoretical simulations is reported, in most studies they follow a common trend with A<G<<C<T i.e. adenine has the lowest electron affinity, thymine the highest.

Atoms/molecules with a low electron affinity value tend to be negatively charged in solution while those with a high electron affinity are positively charged (e.g. Na −53 kJ/mol (positively charged in solution), Cl −349 kJ/mol (negatively charged in solution)). Based on the different electron affinities, it can be assumed that the nucleotides form differently charged ions in aqueous solutions. These different charges in the DNA strand may influence the conducting channel when they are close to the inversion layer thus modulating the source-drain current which in return yields information on the nucleotide sequence. Measuring single charges is rather difficult, especially at room temperature but recent publications have shown that this is possible e.g. if the transistor is operated in the sub-threshold regime.

Tunneling across the nucleotides. Due to their different electron affinity and morphology etc., the tunnel current from source across the nucleotide to drain may be specific for each nucleotide thus revealing the sequence of DNA strands. Tunneling may particularly play a role in devices with very narrow channels where almost the entire channel is obstructed by the pore.

If the channel is so narrow that it is completely obstructed by the pore, the device could operate similarly to a single electron transistor, with source and drain being the contacts, the thin oxide layer in the pore being the barrier and the individual nucleotides representing the 'island' that is charged/discharged.

The discussion above relates to single stranded DNA. In double stranded DNA, each nucleotide of the first strand is connected to its complimentary nucleotide of the second strand (i.e. A to T, and G to C), thus the signal that is measured by the perpendicular gate current (channel modulation or tunneling) yields the combined properties of the pair rather than the individual nucleotides. When sequencing double-stranded DNA, it is possible only to discriminate the two pairs not the individual nucleotides.

The key differentiating features of the device manufactured in accordance with the invention are:

The nanopore is located in the channel of a FET or the island of a single electron transistor.

There is direct modulation of the source-drain current, with no additional conductors and no additional stray capacitances.

Several factors can affect the source-drain current: channel modulation by charged nucleotides, tunneling across nucleotides, nucleotides being part of or acting as the island of a single electron transistor.

Figure 5C:
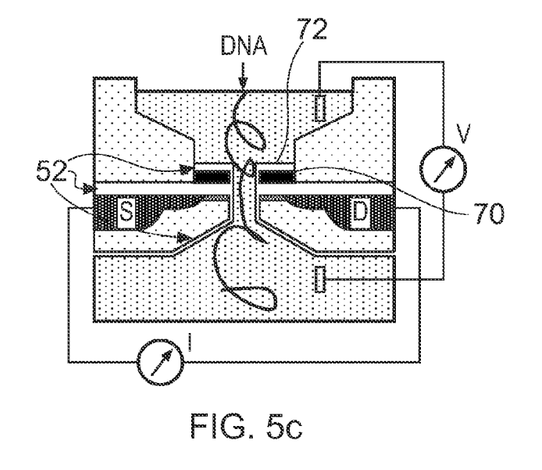

FIG. 5c shows a second example, in which an additional control gate 70 is provided. This is a preferred example, as the structure is then a conventional CMOS transistor.

In addition, this configuration offers control over the gate voltage independently of the voltage applied between the top and bottom chambers. In order to avoid electrochemical reactions if the voltage between control gate and top electrolyte gets too large, the control gate is insulated by a dielectric 72 from the electrolyte, and this is achieved by not completely removing the passivation or inter-metal dielectric layers on top of the control gate. Alternatively the insulating dielectric can be deposited (e.g. PVD, CVD) or grown by electrochemical oxidization of the control gate material. An oxide-less configuration incorporating a metal control gate without gate dielectric (similar to a junction FET (JFET)) is also possible. In principle, the insulation layer on top of the control gate can be omitted. Theoretically, the deposition/growth of the gate dielectric 52 in FIG. 5a is also not necessary and the gate can be contacted directly by the electrolyte (a thin chemical oxide forms automatically).

Figure 5D:
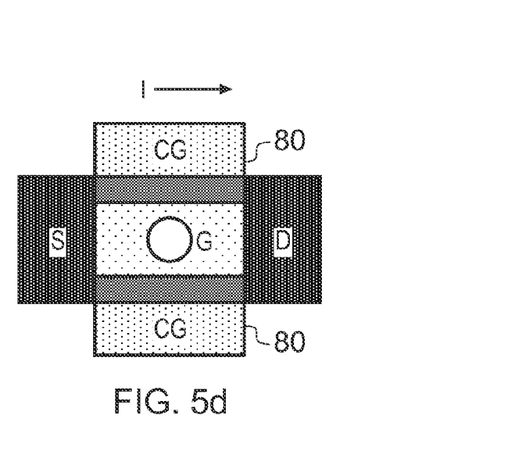
Figure 5E:
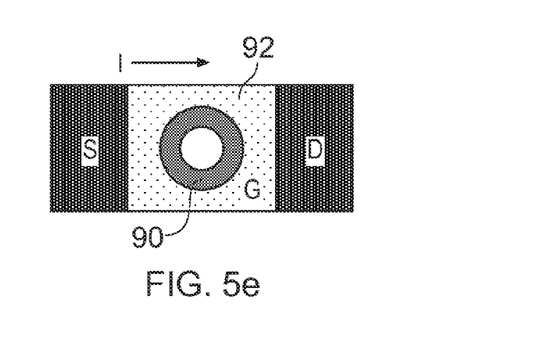

FIGS. 5d and 5e show variations which again depart from a conventional transistor design but which are intended to be within the scope of the invention.

FIG. 5d shows the top view of a similar device but with two separate control gates 80 (CG). In this configuration, a substantial part of the gate is contacted by electrolyte (e.g. water) while its outer rims are covered by the two control gates. Depending on the voltages applied between electrolyte and the control gates, the actual channel width can be considerably smaller than the nominal channel width defined by the width of the source-drain contacts (suppression of the inversion channel beneath and near the regions covered by the control gates). This allows much narrower channels than can be made using current technology, and concentrates current flow near the pore region. This increases its relative influence on the overall current. In the most extreme case, the remaining channel is as narrow as the pore i.e. the current must fully flow (tunnel) across the nucleotides. This makes the device similar to a single electron transistor, with the nucleotides playing the role of the island and the oxide at the pore walls being the barrier.

The gate area may again be controlled by an additional (metal) gate processed on top (in-between the two control gates) that is insulated from the electrolyte and the adjacent control gates. Such a configuration allows maximum control over the channel width and inversion layer independent of the electrolyte voltage (not shown).

FIG. 5e shows another example of such a single-electron nanopore FET, with the island 90 and narrow surrounding 'gate' area 92.

The pore is etched right through the center of the island 90 forming the single-electron-transistor. The barrier of the single electron transistor insulating the island from the channel may be formed by different doping of the island versus the surrounding 'gate' area 92, allowing depletion in the island region while it is surrounded by a zone ('main' gate area) with inversion layer, or vice versa. Alternatively, the barrier is simply formed by the oxide layers in the pore. Again, the device can be implemented with or without control gate (in this configuration the control gate would be on top of the 'gate' area 92 and the island in contact with the electrolyte).

Figure 5F:
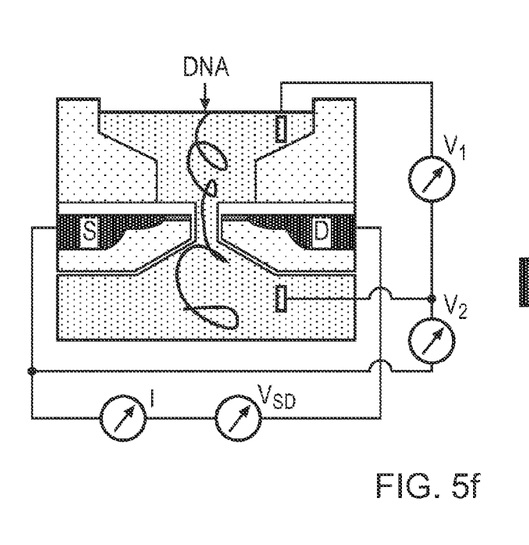

FIG. 5f shows a further embodiment again using tunneling across the junction between the source and drain realized by an extremely narrow channel.

In this example, the pore completely blocks the conductive channel.

The operating principle of such a tunneling device will be explained below.

Figure 6A:
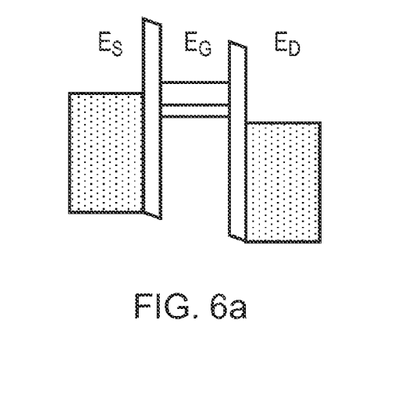
FIGS. 6a to 6b show examples of the energy diagrams in the devices and sample.

The voltages V1 and V2 together define the gate voltage that defines the discrete energetic levels (represented by $E_G$) of the DNA nucleotide in the nanopore with respect to the Fermi energy levels $E_S$ and $E_D$ in the source and drain regions respectively, see the energy diagram in FIG. 6a. $E_G$ can be moved with respect to $E_S$ and $E_D$ by changing V1 and/or V2.

A single nucleotide located in the pore at the height of the conductive channel acts as the 'island' of a single electron transistor, as outlined above. If the energy states of source, nucleotide and drain are correctly aligned, i.e. $E_S \geq E_G$ (i.e. one of the free states there)$\geq E_D$ then resonant tunneling occurs, so that electrons can tunnel from the source across the barrier (which is e.g. the thin oxide layer on the pore wall) onto the nucleotide and from there to the drain.

Figure 6B:
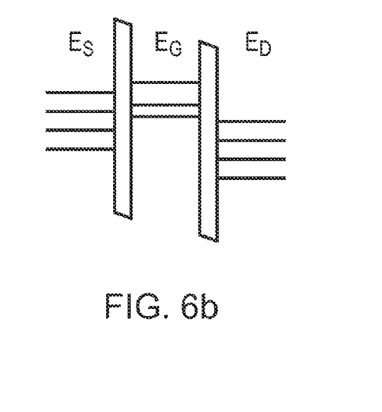

FIG. 6b is an energy diagram which also shows discrete energy levels in the conductive channel.

This arrangement has at least 3 voltage sources; V1, V2 and $V_{SD}$, and another voltage source can be used to control the bulk voltage (not shown).

Different energy states of a nucleotide (represented by the different lines at $E_G$ in FIG. 6a) can contribute to resonant tunneling yielding a specific relation between the current and e.g. the value of V2.

This measurement principle is essentially tunneling spectroscopy. Since the four nucleotides have different energy states, the current-voltage relationship is specific for the individual nucleotides. As the DNA strand is pulled through the pore, the current-voltage characteristic is modulated according to the respective nucleotides passing the conductive channel yielding specific sequence information.

The different examples above show that measurement of transistor currents at fixed voltages (source, drain and gate) can be used or tunnel spectroscopy can be used. By measuring the tunnel currents at different 'gate' voltages (e.g. modulate the bath voltage V2 with respect to the voltage in the device, i.e. shift $E_G$ with respect to $E_S$ and $E_D$ in the energy diagram) more data about the nucleotide in contact with the sensor can be obtained allowing easier and more reliable discrimination between the 4 nucleotides.

The configuration of a pore, coated with thin dielectric layer, with a nucleotide contacted by an inversion layer from either side is similar in effect to a quantum dot or the island of a single-electron transistor. It is a confined system of electrons (here the nucleotide) coupled via tunnel barriers (here the oxide liner of the pore) to macroscopic electrodes (here the inversion layer in contact with source and drain) across which electrons can tunnel in and out of the confined volume. Two processes affect the tunnel current: the addition of electrons to the dot and the excitation of electrons on the dot to higher energy states. The first is governed by the capacitance of the dot and its Coulomb charging. If an electron is added to the dot, its energy increases roughly by $e^2/C$ (C is the capacitance of the dot) causing a blockade in current if the energy in the dot is raised above the potentials of the electrodes. In order for Coulomb blockade effects to be visible at room temperature (thermal energy $k_B T = 25$ mV) the dot capacitance must be sufficiently small ($e^2/C > k_B T$), which is the case for the system proposed.

The second process involves the excitation of electrons within the system yielding an excitation spectrum that is specific to the energy states and therefore to the nucleotide (separation of the energy states in the nucleotides is frequently larger than the thermal energy thus they should be distinguishable at room temperature). In the energy diagram of FIG. 6a, excitation means that an electron is excited from one energy level (line) to a higher energy level (line above)

Transport through quantum dots can also be affected by an external magnetic field. A variety of effects is observed that are based on the addition as well as excitation of electrons. These effects are expected to be different for different nucleotides, providing an additional way to obtain sequence information. In this case, the nanopore is placed in a (time dependent) magnetic field, e.g. between two Helmholtz coils that are connected to an AC current source. Tunnel currents are measured with respect to the magnetic field and the applied voltages.

The key element in the detection principles and devices above is the thin conductive layer with a thickness in the range or smaller than the separation between two adjacent nucleotides in a DNA strand. So far the transistor channel or the 'electrodes' of the tunnel devices are formed by an inversion layer in a semiconducting substrate. Alternatively a two dimensional electron gas (2DEG) that forms at a heterostructure, for example Si/Ge or GaAs/AlGaAs, can be used as conductive sensor layer. An advantage as compared to the inversion layer is that the 2DEG already exists without applying a gate voltage, thus allowing more freedom in setting V1 and V2. Since the 2DEG is at the interface of the two materials and thus remote from the dielectric insulator, the noise is much lower as there is less influence from the trapping/release of charges from interface states at the semiconductor/dielectric interface or other traps in the dielectric.

Moreover, the confinement to the interfacial region results in discrete energy levels in the channel (see FIG. 6b) which may provide increased sensitivity to the device. Discrete energy levels can also be obtained with inversion layers in Si if the Si bulk material is thin enough e.g. <20 nm, as this provides confinement in the z-direction with splitting of the energy bands into discrete states (lines in FIG. 6b). Such layers can be achieved by thinning down the top silicon layer with SOI (silicon-on-insulator) wafers.

A thin conductive layer can also be formed by depleting a highly doped layer from the top and bottom e.g. a pnp structure where both pn junctions are reverse biased such that the n-conducting layer is almost fully depleted except for a thin channel remaining in its middle.

This invention relates to the manufacture of this type of device, and to the resulting device. Most steps for the implementation/manufacturing of the devices above are straightforward. Except for the final steps, they are essentially identical to a state-of-the-art CMOS process (e.g. C065). The final processing steps are to provide a reduced thickness of the stack through which the pore passes and the formation of the nanopore itself.

Figure 7A:
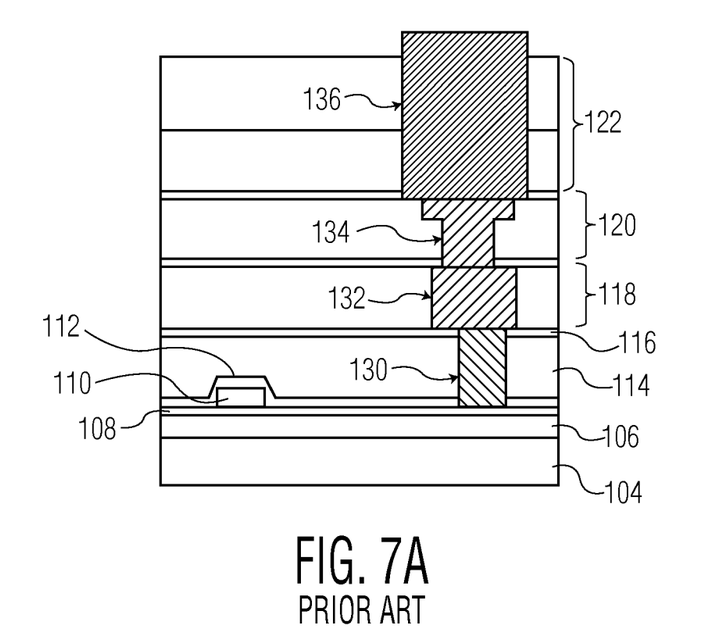
FIGS. 7a and 7b are used to explain a conventional CMOS process.
Figure 7B:
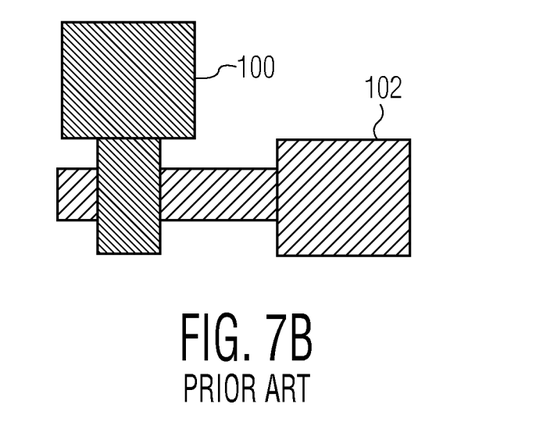

To explain how the method of the invention can be based on existing semiconductor processing techniques, such as CMOS technology, FIG. 7 is used to show a conventional silicon on insulator (SOI) chip with 2 metal layers for interconnects and a passivation stack/scratch protection on top. FIG. 7a is a cross section, and the top view in FIG. 7b shows the main components of the transistor; the channel region, gate contact 100 and drain contact 102. The source contact (not shown) is located on the left side.

As shown in FIG. 7a, the structure comprises the substrate 104, buried oxide layer 106 and the silicon device layer 108.

The polysilicon island 110 forms the gate with the gate dielectric underneath (for example $SiO_2$, HfSiON, not shown). Gate, gate contact and source drain regions are usually covered by a metal silicide to reduce the resistance.

A silicon nitride layer 112 (diffusion barrier) forms the pre metal dielectric together with the silicon oxide dielectric layer 114 which also provides planarisation before the first metal layer 118. There is a further metal interconnect layer 120 in the form of a silicon oxide dielectric layer and a hard mask layer or barrier layer on top, for example SiCN or SiCO.

A passivation stack/scratch protection layer 122 is at the top of the structure, for example SiN on top of $SiO_2$.

Electrical connection from the transistor to the bond pad (at the top surface of the structure) is established with a tungsten via 130 in the pre metal dielectric 114, a Cu layer 132 in the first metal stack 118, a Cu via and layer 134 in the second metal stack 120 and an AlCu plug 136 in the passivation stack 122.

Liners and barrier layers are not shown for simplicity; also the dielectric layers may vary depending on the actual process technology.

The essential feature of this invention is to add an additional interconnect structure, which may be considered as an etch dummy, directly on top of the gate. This is done together with, i.e. at the same time as, the processing of the electrical connections, thus no additional process steps are required.

Figure 8A:
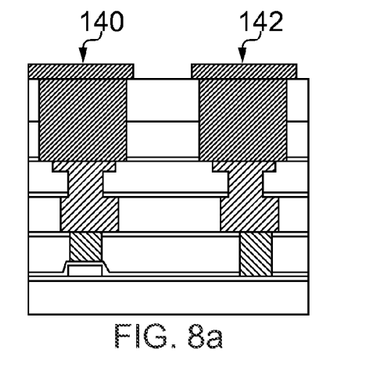
FIGS. 8a and 8b are used to explain the modification to a conventional CMOS process in accordance with the invention.

FIG. 8a shows the interconnect structure 140 formed over the gate in addition to the structure 142 of FIG. 7a.

The device in FIG. 8a has a source region, a drain region and a gate contact region on the substrate. The gate contact region is away from the channel region as shown in FIG. 7b (the channel region is at the cross over in FIG. 7b).

Figure 8B:
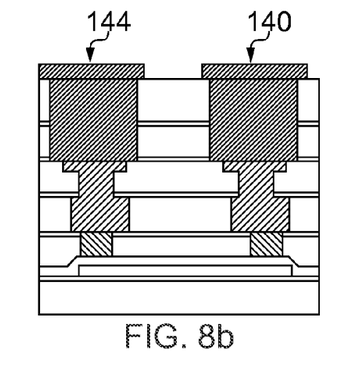

There is at least one filled via through the insulator stack over the source and drain region and gate contact. In addition, FIG. 8 shows a second filled via over a gate contact region (so that the electrical potential of the gate can also be controlled, as explained above). These are conventional connection structures to the transistor. In addition, a third filled via (of the invention) 140 is provided through the insulator stack over the gate channel region. This gate channel region is directly on top of the channel and thus corresponds to the location where the nanopore is to be formed.

FIG. 8b is a cross section along the gate contact and shows the gate via 144 and the additional third via 140. The formation of the additional third via 140 only requires adjustments in the device layout but the CMOS processing is exactly the same.

FIGS. 8a and 8b thus together show the drain contact, gate contact and additional via down to the gate directly on top of the channel. There will also be a contact via to the source and also to the bulk. The full set of vias is not shown in any drawing so that the drawings can be kept simple. As mentioned above, a gate contact may not be required by the end device. Even in this case, a gate contact via can be provided and filled, but the gate can be left unconnected. This enables standard processes be used.

FIGS. 9a to 9d show an exemplary process flow for selective removal of the etch dummy to provide access to the gate from the top of the device. FIGS. 10a and 10b show how to open access from the reverse side of the substrate.

The structure shown in FIGS. 8a and 8b is subjected to a planarisation step (optional), and a hard mask layer is deposited on top of the planarised structure.

Figure 9A:
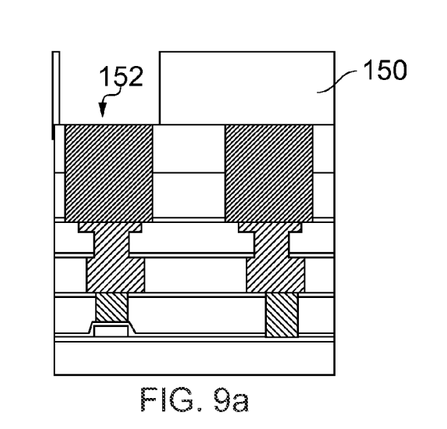
FIGS. 9a to 9d show the additional processing steps of the invention.
Figure 9B:
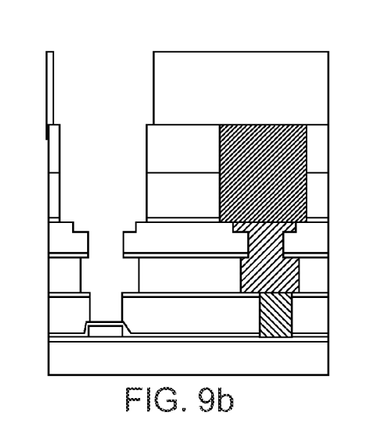
Figure 9C:
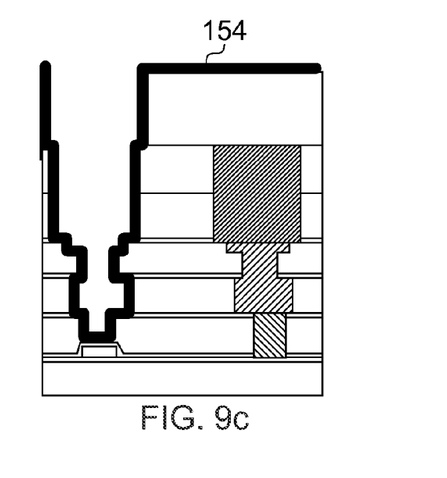
Figure 9D:
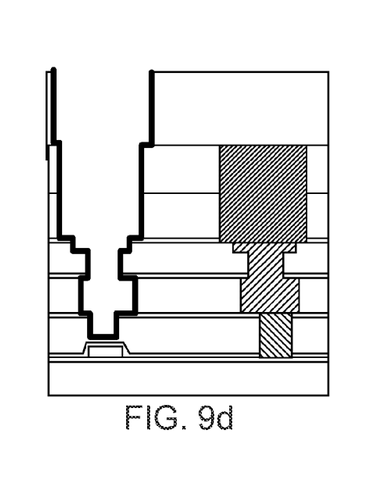
Figure 10A:
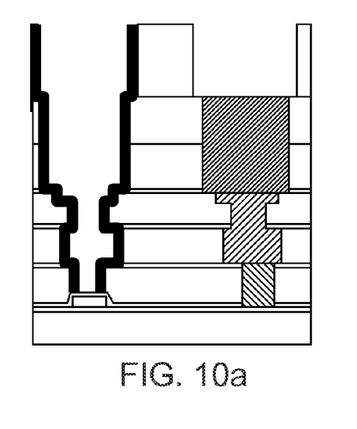
FIGS. 10a and 10b show further additional processing steps for local thinning of the substrate.
Figure 10B:
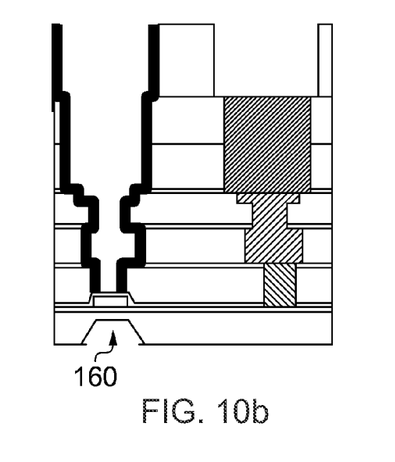

FIG. 9a shows the hard mask layer 150, with an opening 152 defined. The metal layers are selectively removed as shown in FIG. 9b. A dielectric liner 154 is provided as shown in FIG. 9c, and this is (optionally) selectively etched as shown in FIG. 9d.

To keep the description clear and simple, a conventional SOI device is shown with only 2 metal interconnect layers. FIG. 8 shows the chip after full manufacturing (before grinding and dicing) with a standard CMOS process.

The possible further processing steps are thus:
  planarization of the AlCu contacts for better deposition and patterning of the hard mask 150. This is an optional step.
  hard mask deposition, for example a SiN layer (by CVD, PVD etc.) and patterning using lithography, and a hard mask etch.
  selective removal of the metal filling the 'etch dummy' structure by dry or wet etch. This is relatively easy since all surrounding materials are dielectrics, so that etches with good selectivity are available. For example, W can be etched by H2O2 which does not attack SiN or SiO2. Ideally, this step also removes the silicide on the gate to facilitate the nanopore etch. An extra wet or dry etch may be required for this.

The diameter of the W via 130 in the pre metal dielectric 114 is considerably larger than the nanopore (e.g. 90 nm for a C65 process). In order to further reduce the diameter, the dielectric liner 154 is deposited conformally for example by CVD or ALD. The liner 154 also serves as a barrier layer against the analyte to be filled into the chamber (explained below). Some processes use porous materials as intermetal dielectric to reduce the dielectric constant and parasitic capacitance. These materials are prone to water uptake and subsequent change in electrical properties, i.e. increase in leakage and capacitance. The barrier layer 154 thus reduces or prevents water uptake.

An optional anisotropic etch can be applied to remove the dielectric at the bottom of the access opening, right on top of the gate, as shown in FIG. 9d.

The hard mask on top of the bondpads is then removed (by resist deposition, patterning, etch and resist strip) as shown in FIG. 10a to enable electrical contact.

Then, the access structure from the backside is processed as shown in FIG. 10b. This involves deposition of a hard mask (e.g. silicon nitride) on the backside (although this could also be done at an earlier stage before the top access structures are etched) patterning the hard mask and etching the Si substrate wafer e.g. by KOH or RIE to form the locally thinner portion 160. The buried oxide layer (BOX) serves as an etch stop. In order to reduce the etch time, the wafer may be thinned down by grinding beforehand. FIG. 10*b* is a cross section of the device after processing the top and bottom access structures.

The pore is manufactured by a wet etch process, either on the entire wafer or with single dies.

Figure 11A:
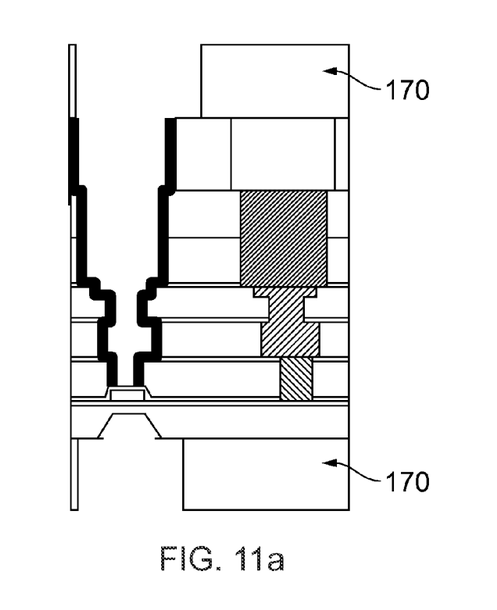
FIGS. 11a to 11c are used to explain possible nanopore etching processes.

To perform the nanopore etch, first fluidic chambers 170 are attached on either side of the wafer/die, as shown in FIG. 11*a*. They can be temporary only for the nanopore etch or permanent to be further used during device operation. The chambers may consist of silicone (PDMS etc), plastic, glass, or resist.

The chambers are for example attached by adhesion, gluing, ultrasonic welding or resist deposition and patterning (e.g. SU-8). Liquid etchant (e.g. diluted hydrofluoric acid) is then applied followed by the main etch process. Two different methods are applicable:

(i) Electrochemical Etching (Optionally Assisted by Light-Photo Electrochemical Etching).

Figure 11B:
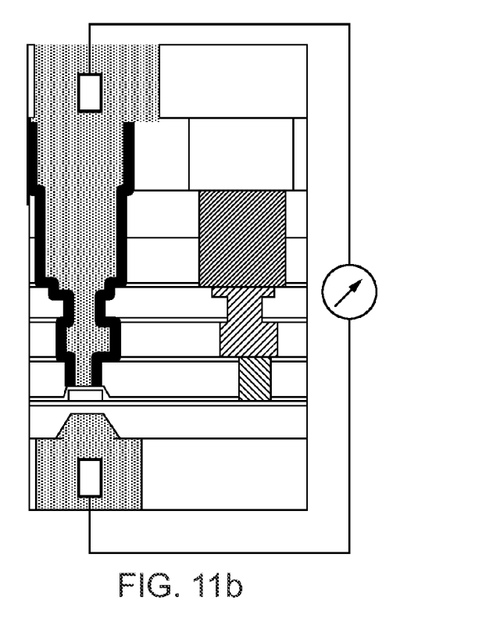
Figure 11C:
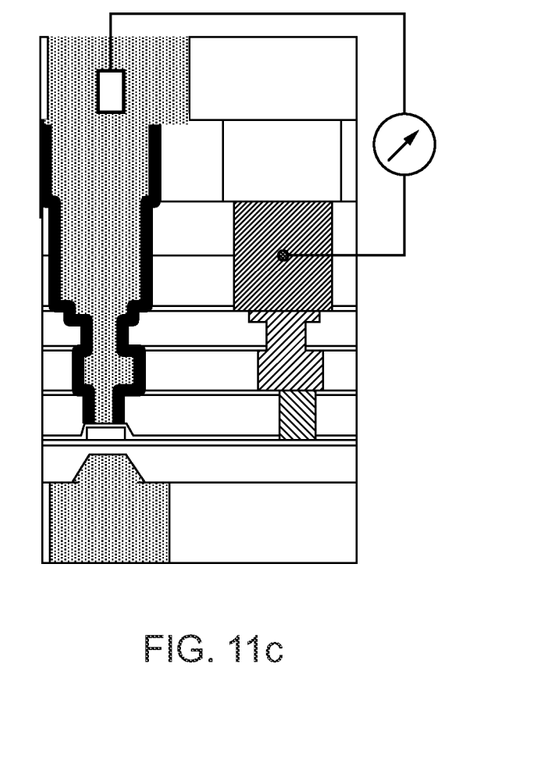

This technique is frequently used to prepare porous silicon. In this process, it is used for etching a single nanopore. The top access structure (etched via in the pre metal dielectric with dielectric liner) serves as etch mask defining the location of the pore on the gate. Again there are two suitable configurations/methods:

In the classical electrochemical etch configuration shown in FIG. 11*c*, the substrate (here gate stack and Si device layer) is positively biased with respect to the etch solution. The potential of the etch solution is controlled by a potentiostat with two electrodes in the liquid, namely a counter electrode and a reference electrode (only one shown in the figure), with the substrate being the working electrode.

The etch process stops as soon as the pore reaches the non conductive buried oxide (BOX). The BOX is removed in a subsequent step (Hf), the pore then connects both liquid reservoirs on either side of the die. As for the fabrication of porous silicon, the etch process may be assisted/enhanced by light.

FIG. 11*b* depicts another configuration for pore etching; both chambers are filled with etchant and contacted by electrodes while the device potential is floating or connected to another voltage source (not shown). A voltage source is applied between both electrodes. The etch process can be controlled by measuring the current between the electrodes. As soon as a pore connects both reservoirs the current increases and the voltage can be turned off to minimize overetch and keep the pore diameter as small as possible. Besides this active control, a passive etch stop mechanism can be implemented with two different electrolytes in the reservoirs e.g. an etchant (Hf solution) in the top reservoir and a quenching solution (e.g. CaCl) in the bottom reservoir. Once the pore is etched and connects both reservoirs the quenching solution inhibits the etchant's activity and prevents further etch and increase in pore diameter. This passive etch stop can be combined with electrode current feedback. Moreover, the process may be assisted by light which can also be controlled (turn light on/off) by the electrode currents.

FIGS. 11*b* and 11*c* show simplified electrode designs and no potentiostat; this is more simple but the liquid potential may be less defined for example due to resistance at the liquid/electrolyte interface.

(ii) Particle Trace Etching

This process is based upon the increased etch rate in an area impacted by high energy ion beams as compared to the surrounding area. The ions damage the material's crystal structure by breaking chemical bonds or by displacing entire atoms (Rutherford scattering) which causes an increased etch rate along the path of an impacting particle. At sufficiently high energies, the path can be very long (several micrometers) providing an excellent trace for etching high aspect ratio nanopores. The high energy implant may be done at several stages during the opening of the top access structures e.g. after the conformal deposition of dielectric or after its removal at the bottom of the access opening, after the hard mask opening on the bondpad or after opening the backside access structure.

The implant dose must be such that only a single ion is implanted in the narrow opening on the gate.

The energy must be high enough for the ion to travel through the gate stack, Si device layer and buried oxide yet low enough that the passivation stack can serve as mask protecting the underlying metal layers. Alternatively, an additional (resist) mask is applied before the implant that covers everything except the top access structure. Ideally the implant energy is chosen such that ions hitting the sides walls of the opening (dielectric liner) do not reach the channel region. Ions should behave electrically neutral e.g. H or noble gas ions.

After all preparations (opening of the access structures, implant and attachment of the fluidic chambers) the chambers are filled with the etchant to etch a small nanopore along the ion's trace (timed etch). Again different solutions may be used on either side, one etching solution and one quenching solution.

A combination of trace etching and electrochemical etching can be used, with optional feedback by electrode currents.

After the pore etch, the device is thoroughly cleaned/flushed to inhibit further etch or corrosion.

The detailed processes required will be apparent to those skilled in the art, and outline descriptions of the processes have been given. Some embodiments may not need all steps of a standard CMOS flow. There are many other ways to produce the devices which will be routine to those skilled in the art.

The description above is limited to features and processes for MOSFETs. However, the dielectric layer of these devices with its large number of surface and interface charges and traps cause considerable noise which may prevent the detection of the weak signals from the nucleotides. In order to minimize this noise, JFETs can be used. The gate is then directly contacted by a metal thus avoiding any oxides and their specific problems. Again the metal can be contacted and controlled by the electrolyte or a separate (gate) contact.

The invention is of particular interest for sequencing of DNA and other (bio) polymers or proteins. Although only single pores have been discussed above, CMOS process technology allows the manufacturing of large arrays of nanopore FETs enabling massive parallel sequencing at high speed. Moreover signal conditioning circuits such as amplifiers, filters and ADCs (analog to digital converter) may be implemented on the same chip/die in close proximity to the sensor device. This prevents signal loss e.g. in the otherwise long connection lines to external amplifiers and can be essential for the detection of the small signals with a sufficient signal-to-noise ratio. Such circuits may be crucial for the detection of individual nucleotides and sequencing of DNA.

In order to obtain a good I-$V_{SD}$ spectrum, each nucleotide should remain in contact with the 'sensor' to allow signal averaging to reduce noise or, in case of tunnel spectroscopy, to allow the current spectrum to be measured in a certain voltage ($E_G$) range. The 'residence' time of each nucleotide at the sensor can be increased/controlled by modulating $V_1$ for example using a square wave or saw tooth voltage, and superposing these on a DC voltage. A feedback loop can be used to control the movement of nucleotides through the pore according to the current measurements.

The device of the invention can have fluid chambers which are part of a micro fluidic system transporting the DNA and electrolyte to the detector device. Signal conditioning circuits can also be provided, such as amplifiers, filters and ADCs (analog to digital converters) on the same chip. These signal conditioning circuits can be used to improve the Signal-to-Noise ratio of the detected signals. A device can incorporate several of the individual detector devices on a single chip/die.

The invention enables the combination of nanopore sensors with complex integrated circuits (e.g. for data processing) on a single die.

Various modifications will be apparent to those skilled in the art.

The invention claimed is:

1. A method of fabricating a detector device, comprising:
    forming a source region, a drain region and a gate contact on a substrate, with a channel region between the source and drain regions;
    forming an insulator layer over the substrate;
    forming first vias through the insulator layer and filling the vias with conductor material, wherein the first vias are provided over the source, drain regions and gate contact,
    wherein the method further comprises:
    forming an additional via through the insulator layer over a gate channel region which is on top of the channel region, and filling the additional via with said conductor material;
    removing the conductor material filling from the additional via to form a first chamber leading to a first side of the gate channel region,
    and wherein the method further comprises etching a nanopore from the first chamber through the channel region.

2. A method as claimed in claim 1, wherein the nanopore is etched through to the opposite side of the substrate.

3. A method as claimed in claim 2, further comprising locally thinning the substrate at the gate channel region to form a second chamber opposite the first chamber.

4. A method as claimed in claim 1, further comprising:
    forming fluid chambers on opposite sides of the nanopore and filling them with electrolyte;
    connecting drive means to the fluid chambers;
    connecting drive means to the source and drain regions and gate contact; and
    providing a current sensor for sensing a charge flow between the source and drain regions.

5. A method as claimed in claim 1, further comprising forming a dielectric liner in the first chamber before etching the nanopore.

6. A method as claimed in claim 5, further comprising etching the dielectric liner to remove a portion of the dielectric liner at the location where the nanopore is to be formed.

7. A method as claimed in claim 1, wherein the nanopore is formed by a wet etch process.

8. A method as claimed in claim 7, wherein the wet etch process comprises electrochemical etching.

9. A method as claimed in claim 1, wherein the nanopore is formed by particle trace etching.

10. A method as claimed in claim 1, wherein forming an insulator layer comprises forming a stack of insulator layers and conductor layers, thereby providing multiple isolated conductor layers.

11. A detector device, comprising:
    a substrate;
    a source region, a drain region and a gate contact on the substrate;
    a channel region between the source and drain regions;
    a gate on top of the channel region;
    an insulator layer over the substrate;
    first vias through the insulator layer filled with conductor material, wherein the first vias are provided over the source and drain region and gate contact,
    an additional via through the insulator layer over the gate, the additional via defining a chamber leading to a first side of the gate channel region,
    a nanopore which passes through the channel region, and which connects fluid chambers on opposite sides of the nanopore;
    a driver for providing a voltage bias between the fluid chambers;
    a driver for providing a voltage between the source and drain regions and gate; and
    a current sensor for sensing a charge flow between the source and drain regions.

12. A device as claimed in claim 11, wherein the nanopore passes through the substrate.

13. A device as claimed in claim 11, wherein the substrate has a locally thinner region in the vicinity of the nanopore.

14. A device as claimed in claim 13, wherein the locally thinner region has a thickness of less than 200 nm.

15. A device as claimed in claim 11, wherein the nanopore has a diameter of less than 10 nm.

* * * * *